United States Patent [19]

Oglevee et al.

[11] Patent Number: 4,897,957
[45] Date of Patent: Feb. 6, 1990

[54] **PRECISION FLOWERING OF REGAL PELARGONIUMS (*PELARGONIUM XDOMESTICUM*)**

[75] Inventors: J. Robert Oglevee; Richard Craig, both of Connellsville, Pa.

[73] Assignees: Oglevee, Ltd.; Research Corporation Technologies, Inc., ; a part interest

[21] Appl. No.: 180,471

[22] Filed: Apr. 12, 1988

[51] Int. Cl.$^4$ .............................................. A01H 3/02
[52] U.S. Cl. ........................................ 47/58; 800/200; 800/DIG. 22; 800/DIG. 67; 47/DIG. 6
[58] Field of Search .................. 47/58, DIG. 6; 800/1

[56] References Cited

U.S. PATENT DOCUMENTS

P.P. 6,080  1/1988  Kirmann ........................... Plt./68

OTHER PUBLICATIONS

Hong, Y. P. et al. (1986) "Effects of Growth Retardants and Shade Levels on the Growth and Flowering of Hybrid Geraniums (*Pelargonium x hortorum* Bailey)" *J. Kor. Soc. Hort, Sci.* vol. 27, No. 1, pp. 66–72.
Thorn-Horst, H., et al., (1977) "a Virus-indexing tissue culture system for geraniums" *Florists' Review* vol. 160, No. 4148, pp. 28,29 and 72–74.
Nilson, J. H. (1975) "Factors Affecting Flowering in Regal Pelargonium (*pelargonium x domesticium* Bailey)" *Acta Horticultural* vol. 51, pp. 299–309.
Erickson, L. E., et al (1980) "The Effect of Cumulative Photosynthetically Active Radiation on the Growth and Flowering of the Seedling Geranium *Pelargonium x Hortium Bailey* " *HortScience*, vol. 15, No. 6, pp. 815–817.
Brickford E. D. et al (1972) "1 characteristics of Light; 2 Fundamentals of Photochemistry" *Lighting for Plant Growth* The Kent State Press pp. 1–14.
White, J. W. et al (1988) "Temperature and Light Integral Effects on Growth and Flowering of Hybrid Geraniums" *J. Amer. Soc. Hort, Sci.*, vol. 113, No. 3, pp. 354–359.
Hackett, W. P., et al (1974) "Flower Induction of *Pelargonium Domesticum* Bailey w'Lavender Grand Slam'-with Exposure to Low Temperature and Light" *Hort Science* vol. 9, No. 1, pp. 63–65.
Vetanovitz, R. P., et al. (1985) "Influence of Four Cultural Systems upon Geranium Stock Plant Productivity" *HortScience* vol. 20, No. 4, pp. 703–705.
White, J. W. et al (1984) "Growth and Development of Geranium to Temperature, Light Integral, $CO_2$ and Chlormequat" *J. Amer. Soc. Hort Sci.* vol. 109, No. 5, pp. 728–735.
Hausbeck, M. K., et al. (1987) "Variation in Resistance of Geranium to *Pythium ultimum* in the Presence or Absence of Silver Thiosulfate" *HortScience*, vol. 22, No. 5, pp. 940–944.
Quatchak, D. J. et al (1986) "Temperature Supplemental Lighting and Chloromequat Chloride Effects on Flowering of Geranium Seedlings" *J. Amer., Soc. Hort. Sci.*, vol. 11, No. 3, pp. 376–379.
Anon, (1963) *Fluorescent Lamps* Bulletin 0-262 Sylvania Lighting Products of General Telephone & Electronics, Issued by the Commercial Engineering Dept., Salem. Mass.
Harthun, Ed, et al, "Geranium (*Pelargonium hortorum*)" *The Ball Red Book* (13th Ed) 1975 Geo. J. Ball Inc. pp. 331–340.
Laurie, A., et al, "Geranium (*Pelargonium hortorum-Geraniaceal*)" *Commercial Flower Forcing* (7th Ed) 1969 McGraw-Hill Book Co., N.Y. pp. 471–480.
"Photons, Flux, and Some Light on Philology," M. G. Holmes et al., *HortScience*, vol. 20(1), pp. 29–31, Feb. 1985.
"Photometric, Radiometric, and Quantum Light Units of Measure: A Review of Procedures for Interconversion," R. W. Thimijan et al., *HortScience*, vol. 18(6), pp. 818–822, Dec. 1983.
"Horticultural Lighting Design," Engineering Bulletin 0-361, GTE Products Corporation, Sylvania Lighting Center.

*Primary Examiner*—James R. Feyrer
*Attorney, Agent, or Firm*—Webb, Burden, Ziesenheim & Webb

[57] ABSTRACT

The precision flowering of Regal Pelargoniums includes the following six stages: the production of pathogen indexed Mother Block and selection phase, the stock plant production phase, the vegetative propagation phase, the floral initiation phase, and the finishing and post-harvest phases. By means of temperature control and misting during vegetative propagation, careful control of temperature and accumulated light during floral initiation, and night-break lighting during finishing if necessary, flowering Regal Pelargoniums may be produced any time during the year. Moreover, as a result of the combined method steps of the present application, the production of a finished, flowering plant from a stock plant cutting may be completed in a total of 13 to 16 weeks.

13 Claims, No Drawings

PRECISION FLOWERING OF REGAL PELARGONIUMS (*PELARGONIUM XDOMESTICUM*)

FIELD OF THE INVENTION

The present invention relates to floricultural methods which bring about the flowering of Regal Pelargoniums (Pelargonium Xdomesticum) at any preselected time throughout the calendar year.

INTRODUCTION

Regal Pelargoniums, or Martha Washington Geraniums, are botanically called *Pelargonium xdomesticum* in the U.S. and *Pelargonium grandiflorum* in much of Europe. Regal Pelargoniums enjoyed extreme popularity for most of the 19th Century; popularity later waned primarily because Regals were difficult to produce on demand as a competitive product. When available, however, Regal Pelargoniums continue to enjoy widespread popularity, especially for particular holidays throughout the year including Easter and Mother's Day.

Although some inroads have been made by researchers, the production of Regal Pelargoniums has predominantly tracked the seasons to yield finished plant products primarily only in the spring months. As a result, until the development of the present process, many markets for Regal Pelargoniums were significantly under-exploited. Notwithstanding certain prior art methods for expediting flowering under conditions of reduced light and temperature (see W. P. Hackett, J. Kister and A. T. Y. Tse, *Flower Induction of Pelargonium domesticum Bailey cv. Lavender Grand Slam with Exposure to Low Temperature and Low Light Intensity*, University of CA, 1974), no process has previously been developed whereby the onset of flowering of Regal Pelargoniums may be controlled any time during the calendar year. A need remains, therefore, for a method for the precision flowering of Regal Pelargoniums at any time such plants are required.

BRIEF DESCRIPTION OF THE INVENTION

In order to meet this need, the present process for the precision flowering of Regal Pelargoniums includes the following six phases: the production of pathogen indexed Mother Block and selection phase, the stock plant production phase, the vegetative propagation phase, the floral initiation phase, and the finishing and post-harvest phases. By means of temperature control and misting during vegetative propagation, careful control of temperature and irradiance during floral initiation, control of temperature and lighting during finishing, and silver thiosulfate treatment during post-harvest, flowering Regal Pelargoniums may be produced at any time during the year. Moreover, as a result of the combined method steps of the present application, the production of a finished, flowering plant from a stock plant cutting may be completed in a total of 13 to 16 weeks.

DETAILED DESCRIPTION OF THE INVENTION

The present method for the precision flowering of Regal Pelargoniums comprises the six phases of (1) Mother Block; (2) stock plant production; (3) vegetative propagation; (4) floral initiation; (5) finishing; and (6) post-harvest treatment. Each phase is discussed individually below.

The *Mother Block Phase* is the stage of the present invention in which Pathogen-Indexed ™ stock plants are generated and selected for use. Although processes for preparing disease-free stock plants are known, the following is exemplary of these processes.

A Regal Pelargonium plant is chosen which has been selected through several generations and has a history of desirable horticultural characteristics. A cutting is taken from that plant and is then Culture-Indexed for various bacterial and fungal pathogens.

After four weeks of thermotherapy at 100° F. day, 95° F. night, with a 16-hour light period, 0.5 mm microcuttings or "meristem-tips" are excised and grown in vitro for eight weeks at 74° F. during a 16-hour day, and 69° F. night. The in vitro growing media is sensitive to *Xanthomonas pelargonii* and *Verticillium alboatrum*, therefore any contaminated tubes are discarded in order to eliminate these bacterial and fungal diseases. Growing plants are then individually planted out of the tube into a sterilized peat-perlite growing medium. When established in a 4-inch Azalea pot the pelargonium plants are tested for known viruses using bioassay and enzyme-linked immunosorbent assay (ELISA).

When doing bioassays small young leaves of the growing plants are removed and ground with mortar and pestle in a 0.05 M phosphate buffer solution containing 3% polyethylene glycol 6000, at a 1:5 dilution rate (W:V). The resultant slurry is gently rubbed onto carborundum dusted cotyledons of 'indicator plants' chosen due to their sensitivity to specific viruses. *Cucumis sativus, Vigna sinensis, Chenopodium quinoa,* and *Phaseolus vulgaris* are the indicator plants commonly utilized. The leaves are then rinsed and observed for two weeks watching for the occurrence of small spots or "local lesions" which may or may not become systemic causing a necrotic or chorotic problem in the growing tip of the indicator plants. All reactions are recorded and if any of the plants look suspicious, the sampled pelargonium is discarded.

Another test used is ELISA, a method which utilizes antiserum to a specific virus that has been manipulated to reveal the presence of that virus in a given plant sample colorimetrically. This color intensity is then measured using a densitometer and statistically analyzed to determine if the plant sample is positive. Only plants determined to be negative by both methods of testing are acceptable for foundation stock and continue through the system.

The second phase, *Stock Plant Production*, is the phase in which the product of phase I is developed into stock plants. Stock plant production should, of course, be timed so that cuttings are available when needed, which is usually approximately 7–10 weeks prior to the fifth phase, *Finishing*, discussed below. Approximately 3 months are required to generate a productive stock plant, and proper pinching is required to build the scaffold that will ultimately produce the desired number of quality cuttings. The stock plants should be pinched at 4 weeks (or 6" height) and again as individual shoots reach 6" in length.

Proper choice of growing media is essential in the stock plant production phase. Two essential requirements for a good growing media are sterility and unimpeded drainage. Otherwise, a number of different growing media are suitable for stock plant production, including sterile soil, peat, peat mixed with sterile soil, peat-like media containing granite sand and processed bark ash, bark chips, perlite, vermiculite or combinations of any or all of the above. Optimal pH for the media is between 5.5 and 7.0. Large containers, such as those which hold 4 to 6 liters of medium, may be used as long as they provide adequate drainage. For ideal growth, stock plants are spaced 11 to 13 per square meter, are allowed full light to 800 micromoles per second per square meter, and are kept at 62° to 64° F. night, 68° –75° depending on ambient irradiance during the day, are maintained at 1,000 ppm $CO_2$ and are never subjected to media having a total soluble salts content greater than 1,000 millimhos.

Regal Pelargoniums are sensitive to proper levels of macro- and micronutrients. It is important to maintain proper levels, of these nutrients, to produce cuttings that are in the ideal condition to be propagated. Calcium, phosphorous magnesium and trace elements should be incorporated into the medium prior to planting. The pH should be adjusted by use of $CaCO_3$ (limestone), and if more Ca is needed Gypsum ($CaSO_4$) may be used to add calcium without affecting pH.

After planting, a constant feed program begins with 150 ppm $NO_3$ and 150 ppm K. A monthly soil and tissue testing program is also commenced immediately. Elements and concentrations are adjusted according to the tests to maintain proper levels.

If medium is high quality peat moss with less than 15% mineral soil added, the proper fertility level would be one-half of the published zonal geranium levels as a starting point. The low end of the "normal range" of tissue tests for geraniums are then followed.

Pest control is important during stock plant production, particularly pest control directed toward combatting greenhouse whiteflies and Botrytis blight. Pesticides and fungicides should be applied to the plants on a rotating schedule to prevent the evolution of resistant pest populations.

Botrytis control is critical especially after pinching, plant cleaning or removal of cuttings. Fungicide applications are particularly important on the days prior to and immediately following propagation in order to reduce the chance of Botrytis infection. Maintenance of low relative humidities and adequate ventilation, along with simple sanitation, maximizes the benefits of this and other pest control techniques. 25 The next phase, *Vegetative Propagation*, begins with the harvesting of terminal cuttings from the stock plant. The cuttings, which are treated with a rooting hormone-fungicide mixture, are placed in a well-drained disease-free growing medium, having soluble salts less than 750 millimhos. Rooting hormones and fungicides are known in the art. The vegetative propagation stage permits rooting within 14 days by the simultaneous maintenance of the growth media at 70° to 75° F. and the application of mist, along with $CO_2$ supplementation.

Sufficient misting of the plants is necessary to counteract evapo-transpiration. Usually this involves frequent misting during the first few days of vegetative propagation, with gradual reductions in number of mistings until misting is discontinued after about 10 days.

In contrast with prior art methods which require 4 to 4½ weeks for vegetative propagation, under the conditions as specified the vegetative propagation phase of the present invention requires 2 weeks (14 days) at most. After the 2-week rooting period under the above conditions, an additional week (approximately) of fertilization and disease control immediately follows to establish and acclimate the plants. More particularly, in the third week, the media temperature is reduced to 62° to 65° F., $CO_2$ injection may continue but the mist is discontinued, and the media is supplemented with 75 to 100 ppm nitrogen and potassium, on an "as required" basis.

If larger plants are required, optional pinching may be performed at this time. Pinching will delay the crop 2 to 3 weeks but will result in larger plants.

To initiate the next stage of *Floral Initiation,* the propagated plants are transferred to finishing pots 5" to 6½" in diameter. Floral initiation may be completed over as few as 14 days by maintaining temperature and accumulated light for the total period within predetermined parameters. For example, floral initiation will be complete if the propagated plants are subjected to 28 days of 58° F. temperatures (63° F. absolute maximum during the day) and a total accumulated light (including both natural and supplemental light) for the 28-day cycle of 350 to 425 moles. (Under conditions of somewhat lower temperature within ordinary plant growth parameters, accumulated light need be only in the lower half of the 350 to 425 mole range.) Those skilled in the art also recognize that any supplemental daylight will commence at least about an hour before dusk, and normally a total of a sixteen hour -photoperiod is maintained. For fewer or greater than 28-day cycles, the daily light is adjusted proportionately to yield the same 350 to 425 accumulated moles of light for the entire period. Under natural light in January 5 weeks at 48° F. is needed.

The fifth stage, the *Finishing phase*, is the phase of flower development. Temperature of the finishing area is maintained between 60° F. and a maximum day temperature of 65° F. with full light being allowed to a maximum of 800 micromoles per second per square meter. The plants are subjected to night-break lighting where necessary. In other words, some cultivars require a night-break lighting period, between 10:00 p.m. to 2:00 a.m., at from 4-5 micromoles per second per square meter. Those skilled in the art can easily determine, with minimal experimental trials, which cultivars require this night-break lighting and can implement it accordingly. Under minimal irradiance, supplemental lights may be required. Those skilled in the art also recognize that any supplemental daylight will commence at least about an hour before dusk, and normally a total of a sixteen hour photoperiod is maintained. These finishing conditions are maintained until the point that buds show faintest perceptible color. These conditions allow the completion of the Finishing phase in 6 to 9 weeks. Growth retardants known in the art may be used during this phase.

As a result of the present improvements in the Vegetative Propagation, Floral Initiation and Finishing phases of the present invention, flowering plants may be produced from stock plant cuttings in only 13 to 16 weeks. These 13 to 16 weeks consist of 3 weeks of vegetative propagation, 4 weeks of floral initiation and 6 to 9 weeks of finishing. The optional pinching before floral initiation adds 2 to 3 weeks to this to yield a larger plant.

The final phase, or Post-harvest phase, is directed generally to the preservation of the quality of the plant and to the enhancement of longevity and consumer satisfaction. Many such techniques are known in the art. Additionally, however, Regal Pelargoniums are sensitive to ethylene and, as a result, petal abscission might be the norm for some cultivars without preventive treatment. Silver Thiosulfate (STS) is effective in reducing petal abscission if, for example, it is applied two weeks before anthesis, when the buds first show color. Post-harvest quality can be extended if plants are kept in cool, bright conditions; warm temperatures, low light, moisture stress, and ethylene exposure consistently reduce quality.

A suitable thiosulfate solution may be prepared as follows. A solution containing 2.24 silver nitrate (AgNO$_3$) is dissolved in 100 ml distilled H$_2$O and is added, with stirring, to a solution of 21.24 g sodium thiosulfate (Na$_2$S$_2$O$_3$·5H$_2$O) dissolved in 100 ml distilled H$_2$O, and the combined solutions are carefully transferred to a plastic or glass container. The resultant composition is a STS concentrate which may be stored for 3 months at about 2° C. in a dark place. For use, 3.9 ml of this concentrate is added to 500 ml H$_2$O, and the composition is then sprayed onto the Regals at the time the buds begin to show color. (Spraying should continue, for any given application, until the droplets formed on the leaves enlarge and begin to run off.) Application later than first bud color may result in discoloration of petals; earlier application may reduce the duration of STS effectiveness.

The invention will be more completely explained by means of the following examples.

EXAMPLE I

A healthy Regal Pelargonium stock plant was watered thoroughly and, 24 hours later, a 2" long terminal cutting having 4 leaves was removed from the stock plant with a sterile knife. The cutting was placed in a well-drained disease-free growing medium consisting of 90 percent sterile peat and 10 percent sterile soil contained within a 3" square pot. The medium contained less than 750 millimhos total soluble salts. The 3" square pot was placed, along with a number of other 3" square pots, on a propagation bench which maintained the temperature of the growth medium at 70–75° F. The cutting was misted, until the leaves were covered with a film of water, every 2 minutes for the first 2 days, every 4 minutes for the next 2 days, every 12 minutes for the next 2 days and once every 30 minutes for 4 days thereafter. After 10 days misting was discontinued and after 14 days of growth media temperature maintenance at 70–75° F., the medium temperature was allowed to drop to 62–65° F. The cutting was allowed to establish for 1 week and was given 100 ppm nitrogen and 100 ppm potassium at each watering.

EXAMPLE II

The propagated cutting of Example I was repotted in a 6" Azalea pot. The propagated cutting was subjected to 28 days of 58° F. night temperatures and 62° F. day temperatures and a total accumulated light for the 28-day cycle of 400 moles. After the 28 days elapsed, the plant had grown from a 2" cutting to a 6" plant having 8 leaves and invisible buds.

EXAMPLE III

The 6" plant produced in accordance with Example II was held for 6 weeks under conditions which automatically supplied night-break lighting of 4–5 micromoles per second per square meter between 10:00 p.m. and 2:00 a.m., and a maximum of 800 micromoles per second per square meter during the day, and temperatures below 65° F. In the fourth week, 1 millimho of silver thiosulfate was applied. The surrounding environment was kept free from excess humidity and ethylene pollutants.

Although the invention has been described with reference to specific methods and materials, the invention is to be limited only insofar as is set forth in the accompanying claims. For example, the 58° F. night temperatures during floral initiation reflects a night temperature choice which, in Pennsylvania and similar climates, can be held constant throughout the year with minimized energy expense for heating, ventilation and air conditioning. The Examples therefore reflect this 58° F. night temperature during floral initiation, but the invention is not intended to be so limited. Notably, extensive additional tests completed subsequent to the tests embodied in the Examples, in which identical conditions were imposed except for 57° F. night temperatures during floral initiation, gave results consistent with the disclosure of the specification Examples, supra.

We claim:

1. A method for the precisely timed production of a Regal Pelargonium plant in 13–16 weeks, comprising the steps of:
   vegetative propagation;
   floral initiation; and
   finishing, wherein said floral initiation step further comprises controlling minimum total accumulated light exposure per plant to between 350 to 425 moles.

2. The method of claim 1 wherein said floral initiation step further comprises controlling the night ambient air temperature to about 58° F.

3. The method of claim 1 in which said vegetative propagation step further comprises the maintenance of a growth medium at a temperature between 70° and 75° F.

4. The method of claim 3 wherein said vegetative propagation step further comprises sufficient misting of the Regal Pelargonium plant to prevent moisture loss to evaporation and transpiration.

5. The method according to claim 4 wherein said vegetative propagation is completed over a period of up to 3 weeks.

6. The method according to claim 5 wherein said growth medium for vegetative propagation contains a total soluble salt level having a measured value of less than 750 millimhos.

7. The method according to claim 6 wherein said vegetative propagation step further comprises the maintenance of said growth medium at a temperature of 70–75° F. for two consecutive weeks and the maintenance of said growth medium at a temperature between 62-6° F. for a third consecutive week.

8. The method according to claim 7 wherein said floral initiation is accomplished over a period of between 20 and 35 days.

9. The method according to claim 8 wherein said floral initiation is accomplished in 28 days, with total accumulated light for the 28 day period equal to about 400 moles per plant.

10. The method according to claim 9 wherein said finishing step further comprises limiting the light exposure of the said Regal Pelargonium to a maximum of 800 micromoles per second per square meter per day.

11. The method according to claim 10 wherein said finishing step further comprises the exposure of said Regal Pelargonium to night-break lighting.

12. The method according to claim 11 wherein said finishing step is followed by post-harvest treatment.

13. The method according to claim 12 wherein said post-harvest treatment further comprises contacting said Regal Pelargonium plant with silver thiosulfate.

* * * * *

UNITED STATES PATENT AND TRADEMARK OFFICE
CERTIFICATE OF CORRECTION

PATENT NO. : 4,897,957
DATED : February 6, 1990
INVENTOR(S) : J. Robert Oglevee and Richard Craig It is certified that error appears in the above-identified patent and that said Letters Patent is hereby corrected as shown below:

Column 2 Line 18 "alboatrum" should read --albo-atrum--.

Column 3 Line 46 delete "25" and being a new paragraph with --The--.

Column 4 Line 26 "-photoperiod" should read --photoperiod--.

Claim 7 Line 48 Column 6 "6" should read --65--.

Signed and Sealed this

Seventeenth Day of March, 1992

Attest:

HARRY F. MANBECK, JR.

*Attesting Officer*  *Commissioner of Patents and Trademarks*